United States Patent
Moradi et al.

(10) Patent No.: US 9,139,547 B2
(45) Date of Patent: Sep. 22, 2015

(54) MULTISTAGE PROCESS FOR PREPARING ALKALI METAL SALTS OF SPECIFIC 4-HYDROXY-2-OXO-2,5-DIHYDROFURAN-3-CARBOXYLIC ESTERS

(71) Applicant: BAYER CROPSCIENCE AG, Monheim (DE)

(72) Inventors: Wahed Ahmed Moradi, Monheim (DE); Christian Funke, Leichlingen (DE); Taraneh Farida, Pulheim (DE); Albert Schnatterer, Leverkusen (DE); Reiner Rosellen, Leverkusen (DE); Volker Brehme, Nottuln (DE); Stefanie Rinker, Huenxe (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/417,260

(22) PCT Filed: Jul. 29, 2013

(86) PCT No.: PCT/EP2013/065904
§ 371 (c)(1),
(2) Date: Jan. 26, 2015

(87) PCT Pub. No.: WO2014/019982
PCT Pub. Date: Feb. 6, 2014

(65) Prior Publication Data
US 2015/0210662 A1    Jul. 30, 2015

(30) Foreign Application Priority Data
Aug. 1, 2012 (EP) .................. 12178859

(51) Int. Cl.
C07D 307/00 (2006.01)
C07D 307/68 (2006.01)
C07C 67/333 (2006.01)
C07C 67/343 (2006.01)

(52) U.S. Cl.
CPC ............ C07D 307/68 (2013.01); C07C 67/333 (2013.01); C07C 67/343 (2013.01)

(58) Field of Classification Search
CPC ....................................................... C07D 307/68
USPC ........................................................ 549/318
See application file for complete search history.

(56) References Cited

U.S. PATENT DOCUMENTS 8,318,955 B2    11/2012 Lui et al.

FOREIGN PATENT DOCUMENTS

| EP | 950653 A1 | 10/1999 | |
|---|---|---|---|
| WO | 2008150487 A2 | 12/2008 | |
| WO | 2009036899 A1 | 3/2009 | |
| WO | WO 2009036899 * | 3/2009 | .......... C07D 307/68 |
| WO | 2011018180 A1 | 2/2011 | |
| WO | 2012117015 A1 | 9/2012 | |

OTHER PUBLICATIONS

International Search Report received in corresponding PCT/EP2013/065904, mailed Aug. 23, 2013.
Benary, "On the action of halo fatty acid halides on malonic ester.", II. Synthesis of tetramic acid, BCS07-3115, Jun. 11, 1911, pp. 1-9.
Breslow, "A New Synthesis of b-Keto Esters of the Type RCOCH2COOC2H51,2", vol. 66, Aug. 1944, pp. 1286-1288.
Campbell, Synthesis of (E)- and (Z)-Pulvinones, J. Chem. Coc. Perkin Trans. 1, 1985, XP-001005573, pp. 1567-1576.

* cited by examiner

*Primary Examiner* — Nizal Chandrakumar
(74) *Attorney, Agent, or Firm* — Miles & Stockbridge P.C.

(57) ABSTRACT

The present invention relates to a multi-stage method for preparing alkali metal salts of specific 4-hydroxy-2-oxo-2,5-dihydrofuran-3-carboxylic esters of the formula (I),

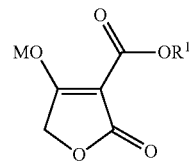

in which M and $R^1$ are as defined in the description,
which proceeds from malonic ester and does not require isolation of intermediates.

9 Claims, No Drawings

MULTISTAGE PROCESS FOR PREPARING ALKALI METAL SALTS OF SPECIFIC 4-HYDROXY-2-OXO-2,5-DIHYDROFURAN-3-CARBOXYLIC ESTERS

CROSS REFERENCE TO RELATED APPLICATIONS

This application is a §371 National Stage Application of PCT/EP2013/065904, filed Jul. 29, 2013, which claims priority to EP 12178859.0, filed Aug. 1, 2012.

BACKGROUND

1. Field of the Invention

The present invention relates to a multi-stage method for preparing alkali metal salts of specific 4-hydroxy-2-oxo-2,5-dihydrofuran-3-carboxylic esters which starts from malonic ester and does not require isolation of intermediates.

2. Description of Related Art

The preparation of hydroxy-2-oxo-2,5-dihydrofuran-3-carboxylic esters, the corresponding tautomers or the alkali metal salts thereof, and also the use thereof as a component in the synthesis of biologically active compounds, is known (WO 2011/018180, WO 2009/036899, J. Chem. Soc., Perkin Trans. 1, 1985, pages 1567 to 1576, Berichte der Deutschen Chemischen Gesellschaft (1911), 44, 1759-1765). However, the known methods have disadvantages as described hereinafter.

WO-A-2012/117015 discloses a method for preparing sodium or potassium salts of 4-hydroxy-2-oxo-2,5-dihydrofuran-3-carboxylic esters. However, the method according to WO-A-2012/117015 is not conducted in the presence of a phase transfer catalyst. Moreover, the method in step (ii) uses the expensive component ethyl chloroacetate to azeotrope the aqueous phase. The partial hydrolysis of ethyl chloroacetate leads to high reactant and disposal costs.

WO 2011/018180 describes a preparation of hydroxy-2-oxo-2,5-dihydrofuran-3-carboxylic ester starting from malonic ester. The latter is reacted with a haloacetyl chloride compound in the presence of a base (see reaction scheme 1). After addition of water, the desired 4-hydroxy-2-oxo-2,5-dihydrofuran-3-carboxylic ester is obtained. The base is selected so as to be capable of deprotonating the malonic ester, as a result of which the enolate of the malonic ester is formed, which is then acetylated by the haloacetyl chloride compound. Suitable bases are especially alkoxides of the general formula $M(OR^a)_b$, in which M is $Na^+$, $K^+$, $Mg^{2+}$, b is 1 or 2 and $R^a$ is methyl or ethyl. Sodium methoxide is specified as preferred. On completion of ring closure, the desired product is obtained together with an inorganic salt which is formed as a by-product (e.g. NaCl if a sodium alkoxide is used as the base).

Reaction scheme 1:

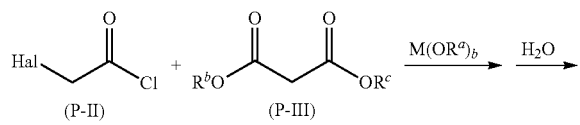

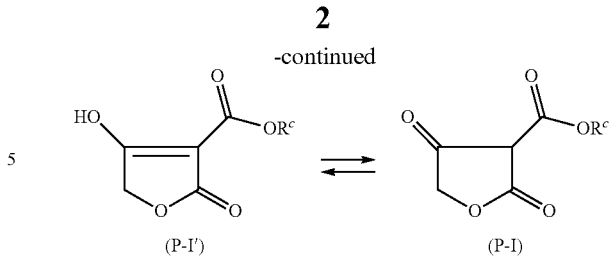

The removal of the inorganic salt from the reaction mixture, especially when it is NaCl, is achievable only through a very high level of technical complexity, if at all, since the compounds of the formulae (P-I') and (P-I) are of very good water solubility. Distillation is impossible since the compounds of the formulae (P-I') and (P-I) decompose at relatively high temperatures with release of $CO_2$. The inorganic salt is therefore not removed. Instead, it is carried over into the subsequent reaction and can only be removed following completion of the further reaction of the compounds of the formulae (P-I') and/or (P-I).

WO 2009/036899 describes a synthesis of salts of 4-hydroxy-2-oxo-2,5-dihydrofuran-3-carboxylic esters, which proceeds from a malonic ester potassium salt and in which the corresponding salt of a 4-hydroxy-2-oxo-2,5-dihydrofuran-3-carboxylic ester is prepared using chloroacetic ester and an alkoxide base, e.g. sodium methoxide (see reaction scheme 2). This reaction does not give rise to any inorganic salts which have to be carried forward. However, it is necessary for their removal to completely remove the polar solvent dimethylformamide (DMF) or dimethylacetamide (DMA) used as solvent in step 1. DMF and DMA are both toxic for reproduction and expensive and are very difficult to remove and recycle. A further disadvantage is the use of the expensive monopotassium salt of malonic ester.

Reaction scheme 2:

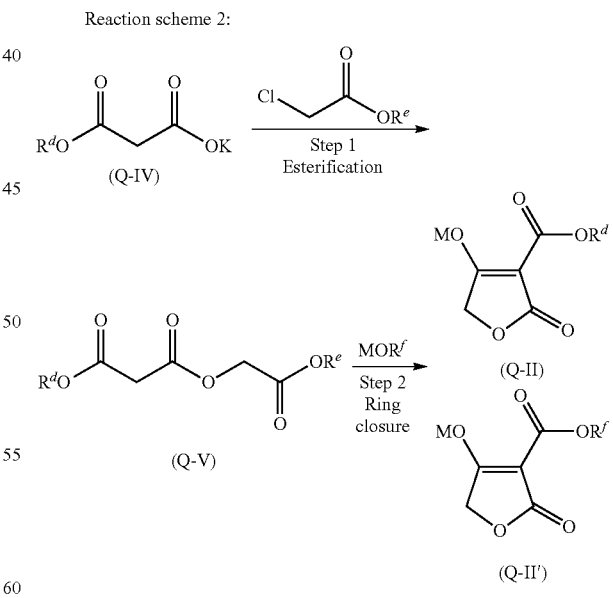

Step 1 of the aforementioned reaction is an esterification in which potassium chloride is obtained as a by-product, which is subsequently removed from the reaction mixture by an aqueous wash. In step 2, the ring closure to give the desired compound (Q-II) takes place, and a transesterification may occur therein, so that the product is obtained as a mixture of the compounds of the formulae (Q-II) and (Q-II'). Compounds of the formula (Q-IV) are solids and are commercially available or can be prepared by known methods (cf. J. Am. Chem. Soc. 1944, Nr. 66, p. 1286, EP-A-950653, WO 2008/150487).

The preparation of the product according to the method cited in WO 2009/036899 is industrially disadvantageous since the method proceeds from expensive malonic ester potassium salts of the formula (Q-IV) present in solid form. In the case of industrial preparation, the use of solids as starting materials is fundamentally undesirable, since the technical handling of solids is difficult and more often involves a change of solvent, which overall leads to a considerable technical complexity for performing the reaction.

SUMMARY

Starting from the known methods for preparing salts of 4-hydroxy-2-oxo-2,5-dihydrofuran-3-carboxylic esters, the object is now that of how these can be simply and cost-effectively prepared, such that the method may also be used for industrial preparation of the desired compound.

It would be particularly desirable to find a method that proceeds from simple starting materials that does not require difficult isolation of intermediates and change of solvents. Simple, cost-effective methods are understood to mean those methods that are conducted without major financial expenditure since the starting materials are, for example, cost-effective and/or have no carcinogenic, mutagenic or reprotoxic activity (CMR activity), the method requires few process steps or is even carried out as a "one-pot reaction" (i.e. isolation of intermediates is not necessary), and/or the desired sodium or potassium salt of the 4-hydroxy-2-oxo-2,5-dihydrofuran-3-carboxylic esters is obtained in a sufficiently high yield and purity. It is further of advantage to provide a method that conserves resources, in which, for example, less energy is needed and/or which is selective, i.e. by-products are only formed in low amounts.

A method has now been found for preparing alkali metal salts, particularly sodium or potassium salts, of specific 4-hydroxy-2-oxo-2,5-dihydrofuran-3-carboxylic esters of the general formula (I), that does not require complex isolation and/or purification of intermediates, and in which the solvent does not have to be changed. Furthermore, in contrast to the prior art, no reprotoxic solvent is required. The method according to the invention is thus particularly simple, resource-conserving and cost-effective to carry out. At the same time, the starting materials used are inexpensive. The method may be conducted either continuously or in batch mode.

It is known that hydroxy-2-oxo-2,5-dihydrofuran-3-carboxylic esters may also be present as tautomers, namely in the form of 2,4-dioxotetrahydrofuran-3-carboxylic esters. Any reference here to hydroxy-2-oxo-2,5-dihydrofuran-3-carboxylic esters accordingly also includes the corresponding tautomer.

The invention thus provides the method described below for preparing an alkali metal salt of a 4-hydroxy-2-oxo-2,5-dihydrofuran-3-carboxylic ester of the formula (I)

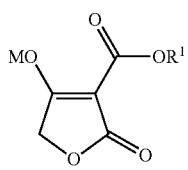

(I)

where

M is an alkali metal, preferably sodium or potassium, and the residue $R^1$ has the meaning stated below, wherein the alkali metal salt of 4-hydroxy-2-oxo-2,5-dihydrofuran-3-carboxylic ester of the formula (I), as previously described, may be present in the following tautomeric forms:

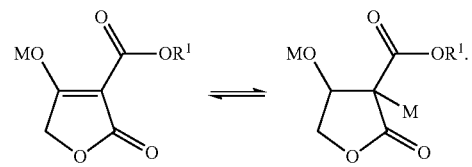

The application accordingly relates to a method for preparing an alkali metal salt, particularly a sodium or potassium salt, of a 4-hydroxy-2-oxo-2,5-dihydrofuran-3-carboxylic ester of the formula (I), comprising the following steps:

Step (i): Reacting a Malonic Ester of the General Formula (II)

(II)

with an alcoholic (preferably methanolic or ethanolic) optionally water-containing alkali metal hydroxide solution, particularly sodium or potassium hydroxide solution, to give the corresponding malonic ester monoalkali metal salt of the formula (III)

(III)

optionally preferably in the presence of an aromatic hydrocarbon compound (aromatic hydrocarbon) as solvent (variant [i-B]) or without solvent with optional subsequent addition of the aromatic hydrocarbon compound (variant [i-A]) to the reaction mixture and preferably removal of the alcohol present in the reaction mixture and optionally the water, wherein the malonic ester mono-alkali metal salt of formula (III) is then present in the aromatic hydrocarbon as a suspension after removal of the alcohol and optionally the water, and wherein the aromatic hydrocarbon present from the start or added after the reaction may serve as an azeotroping agent for removal of water;

Step (ii): Reacting the Malonic Ester Monoalkali Metal Salt of the Formula (III) from Step (i) with a Chloroacetic Ester of the Formula (IV)

(IV)

in the presence of at least one phase transfer catalyst to give a compound of the formula (V)

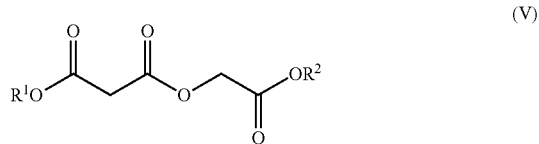

wherein the phase transfer catalyst is an organic ammonium or phosphonium salt,

Step (iii): Reacting the Compound of the Formula (V) by Addition of an Alkali Metal Alkoxide of the General Formula (VI)

$$M'OR^3 \quad (VI)$$

in a ring closure reaction as a result of which the alkali metal salt of 4-hydroxy-2-oxo-2,5-dihydrofuran-3-carboxylic ester of the formula (I) is produced, Usually the residue $R^1$ in the product of the formula (I) originates from the ester used of the formula (II). Furthermore, it is also possible that the substituent $R^1$ originates from the chloroacetic ester used of the formula (IV), from the alkoxide of the formula (VI) or the alcohols present in the reaction. The product obtained of the formula (I) may thus generally be a mixture of more than one product which differ from each other in the substituent $R^1$. If $R^1$, $R^2$ and $R^3$ are different, for example, then three products of the formula (I) can accordingly arise, with $R^1$, $R^2$ or $R^3$ respectively as the corresponding substituent.

$R^1$ and $R^2$ are preferably identical residues (e.g. methyl or ethyl) according to the invention. When $R^1$ and $R^2$ are different, the ring closure reaction in step (iii) can lead to the compounds of the formulae (I) and (I') (see reaction scheme 3).

The same applies also to $R^3$, and $R^3$ should preferably also be identical to $R^1$ and $R^2$, i.e. with particular preference, $R^1$, $R^2$ and $R^3$ are identical.

Reaction scheme 3:

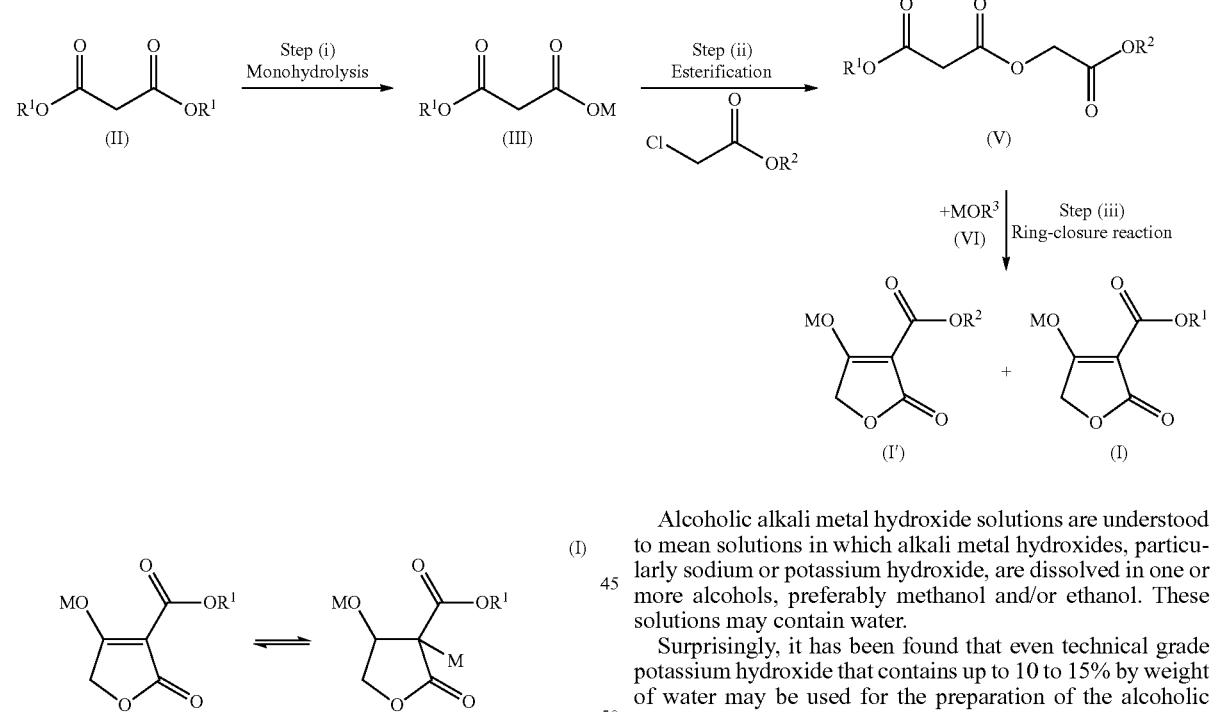

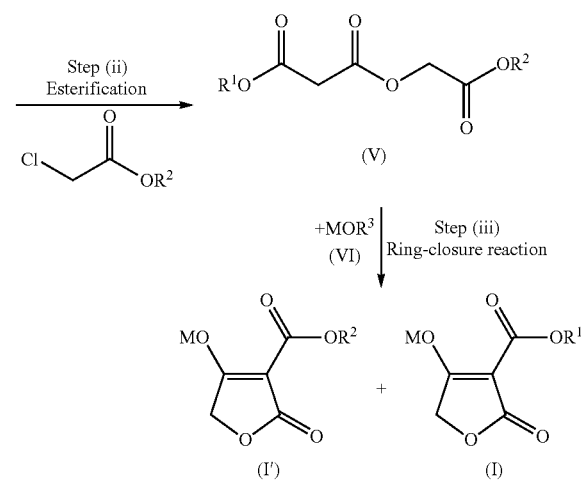

where in the above-mentioned general formulae (I) to (VI)

$R^1$, $R^2$ and $R^3$ are each independently $C_1$-$C_{12}$-alkyl; preferably $R^1$, $R^2$ and $R^3$ are independently of each other $C_1$-$C_6$-alkyl (e.g. methyl or ethyl); and M and M' are each independently an alkali metal, preferably sodium or potassium, in the corresponding oxidation state.

DETAILED DESCRIPTION OF A PREFERRED EMBODIMENT

In a preferred embodiment of the invention, the residues (substituents) $R^1$, $R^2$ and $R^3$ in the general formulae (I) to (VI) are identical. In a particularly preferred embodiment, $R^1$, $R^2$ and $R^3$ in the general formulae (I) to (VI) are identical and are methyl or ethyl.

Alcoholic alkali metal hydroxide solutions are understood to mean solutions in which alkali metal hydroxides, particularly sodium or potassium hydroxide, are dissolved in one or more alcohols, preferably methanol and/or ethanol. These solutions may contain water.

Surprisingly, it has been found that even technical grade potassium hydroxide that contains up to 10 to 15% by weight of water may be used for the preparation of the alcoholic alkali metal hydroxide solution. The appropriate amount of water is then present in the alcoholic potassium hydroxide solution. The inventors have found that it is advantageous in step (i) if a certain amount of water is present in the reaction mixture which is necessary for dissolving the alkali metal hydroxide. The use of dry potassium methoxide in methanol (KM32) is less preferable, in which case water should be added. In the reaction according to the invention, preferred alcoholic alkali metal hydroxide solutions to be used are approximately a 15 to 20% strength methanolic potassium hydroxide solution or approximately a 10% strength methanolic sodium hydroxide solution. For the industrial method, technical grade potassium hydroxide is preferably used for preparing the alcoholic solution. The water content of the alcoholic alkali metal hydroxide solution is preferably 0.01 to 10% by weight, particularly preferably 0.05-5% by weight, particularly preferably 0.1-2% by weight, based on the weight of the solution.

If sodium hydroxide (99%) in alcohol (e.g. methanol) is used, the reaction mixture contains only a small proportion of water. In comparison to a potassium hydroxide solution, a larger amount of alcohol (e.g. methanol) must then be used to dissolve the desired amount of sodium hydroxide. The amount of alcohol to be added, which is necessary to dissolve the desired amount of sodium hydroxide or potassium hydroxide, may be discovered by simple experimentation by those skilled in the art. This amount of alcohol may vary.

The alcoholic alkali metal hydroxide solution is adjusted such that a solution up to 30% by weight, preferably a solution approximately 10% to approximately 20% by weight, is present, based on the amount of alkali metal hydroxide used.

After completion of the reaction in step (i), malonic ester monoalkali metal salt of the formula (III) is reacted without further purification. Prior to this, however, the alcohol and optionally the water present in the reaction mixture are preferably firstly removed from the reaction mixture. This can be carried out, for example, by azeotropic distillation using an azeotroping agent. For this purpose, an aromatic solvent is preferably added as an azeotroping agent to the reaction mixture after the reaction. The azeotroping agent may already be present in the reaction mixture at the start of the reaction, or may only be added after the reaction. Known azeotroping agents are aromatic hydrocarbons, principally toluene or xylene. If the azeotroping agent is not added until after the reaction, xylene is preferably used as azeotroping agent.

The removal of the water optionally present in step (i) may also evidently be carried out by using a water separator. The azeotropic distillation may then be dispensed with.

In the distillation after step (i), it is advantageous not to remove the whole amount of aromatic hydrocarbon compound in order to avoid a deposition of solid malonic ester alkali metal salt of the formula (III) in the reaction vessel (reactor).

As the malonic ester alkali metal salt of the formula (III), (e.g. the malonic ester sodium salt and potassium salt) is insoluble in the aromatic hydrocarbon, a suspension of malonic ester alkali metal salt in the aromatic hydrocarbon is obtained. This suspension may be used directly in step (ii) of the method according to the invention without further processing. The configuration of the reaction in step (i) is extremely advantageous compared to the known methods since preferably the malonic ester monoalkali metal salt of the formula (III) need never be isolated as a pure substance. A technically complex and costly isolation and subsequent drying of the malonic ester monoalkali metal salt of the formula (III) can be avoided.

In one variant [i-A] of step (i), the reaction in step (i) is carried out without solvent, i.e. the reaction is carried out exclusively in the alcohol, which may contain water, introduced via the alcoholic alkali metal hydroxide solution. If desired, the same or another alcohol (preferably methanol and/or ethanol) may additionally be added to the reaction mixture in step (i). The amount of alcohol present in the reaction mixture is gauged such that the reaction mixture remains readily able to be stirred during the reaction in step (i). For reasons of efficiency, only one alcohol is present in the reaction in step (i-A), namely the alcohol which is also used for preparing the alcoholic alkali metal hydroxide solutions. The alcohol used in variant [i-A] may be recovered at the end of the reaction, as described below, and be used again for preparing the alcoholic alkali metal hydroxide solution used in step (i). Owing to this, the variant [i-A] can be carried out in a particularly resource-conserving manner.

On completion of the reaction in variant [i-A] of step (i) and almost complete removal of the alcohol present in the reaction mixture, the water optionally present in the reaction mixture must now be azeotropically removed. For this purpose, an aromatic hydrocarbon compound is added to the reaction mixture as azeotroping agent. Such azeotroping agents are, for example, toluene and xylene, although xylene is preferably used in the variant [i-A]. This is because xylene does not form an azeotrope with the alcohol, particularly methanol, still optionally present, and thus it can be recycled without much difficulty and be used again in step (i).

After completion of the reaction and addition of the aromatic hydrocarbon compound, the reaction mixture is distilled until no more water is present, while taking care that a certain amount of aromatic hydrocarbon compound still remains in the reaction vessel. The proportion of the aromatic hydrocarbon compound should preferably be at least 50% by weight with respect to the monoalkali metal salt of malonic ester of the formula (III).

In another variant [i-B] of step (i), the aromatic hydrocarbon is already present during the reaction in the reaction mixture, and serves as a solvent at the start, and as an azeotroping agent after completion, of the reaction. In variant [i-B], toluene is preferably used. The advantage here is that the proportion of alcohol required in step (i) may be reduced and that the alcohol present in the reaction mixture and the water are simultaneously (azeotropically) distilled off.

In the method according to the invention, there is no solvent change between step (i) and (ii), since the aromatic hydrocarbon compound present at the start or added later in step (i) serves as the solvent in step (ii). Compared to the known methods, this has the advantage that the method can be developed as a one-pot reaction. Costs can therefore be reduced and the method is resource-conserving.

Since the chloroacetic ester used in step (ii) is liquid, it is not strictly necessary to add another solvent in step (ii), in addition to the aromatic hydrocarbon already present.

The phase transfer catalysts (PTC) which may be used in step (ii) are known to those skilled in the art. Preference is given to using just one phase transfer catalyst. However, two or more different phase transfer catalysts may also be used. Particularly suitable phase transfer catalysts used according to the invention are organic ammonium or phosphonium salts, particularly tetraalkylammonium salts, benzyltrialkylammonium salts, tetraalkylphosphonium salts, benzyltrialkylphosphonium salts and also mixtures thereof.

Organic ammonium salts, particularly tetraalkylammonium salts and benzyltrialkylammonium salts, are preferably used in the method according to the invention. Such salts are, e.g, tetra-n-butylammonium chloride or bromide, tetra-n-butylammonium hydrogen sulphate, tri-n-butylmethylammonium chloride or bromide, tri-n-butylmethylammonium hydrogen sulphate, benzyltriethylammonium chloride or bromide, benzyltriethylammonium hydrogen sulphate, trioctylmethylammonium chloride or -bromide and trioctylmethylammonium hydrogen sulphate.

Particular preference is given to using the commercially available tetra-n-butylammonium chloride or bromide and also the commercially available trioctylmethylammonium chloride in step (ii).

The phase transfer catalyst is used in catalytic amounts and can be determined by those skilled in the art by routine experiments.

It is advantageous, however, if the amount of phase transfer catalyst used in step (ii) is in the range from approximately 0.01 to approximately 30 mol %, based on the monoalkali metal salt of the formula (III). Preferably the amount is in the range from approximately 0.05 to approximately 5, particularly preferably in the range from approximately 0.1 to approximately 3 mol %, based on the monoalkali metal salt of the formula (III).

Step (ii) can be carried out under mild reaction conditions. This has the advantage that a lower level of by-products are formed and the reaction mixture may be worked-up easily, which in turn leads to higher yields of the desired target product.

The use of a phase transfer catalyst makes it possible to carry out the reaction according to the invention in a one-pot procedure and essentially without a change of solvent.

One advantage of the configuration of step (ii) of the method according to the invention is also that the unreacted chloroacetic ester of the formula (IV) is available without further work-up for a fresh reaction with the compound of the formula (III), which is a major advantage for the continuous method, when desired.

The compound of the formula (V) obtained in step (ii) is also obtained in such a purity that it may be used without further isolation in step (iii).

However, it is preferable to remove the alkali metal salt from the reaction mixture containing the compound of the formula (V) before further reaction in step (iii). This is possible using all methods according to the prior art. It is preferable to subject the reaction mixture to a filtration or a water wash in order to remove the alkali metal salt formed in step (ii), particularly sodium chloride or potassium chloride. Should it be necessary, the water present due to the water wash may be removed azeotropically, as described in step (i).

For the ring closure reaction in step (iii), any alkali metal alkoxide may be used, particularly sodium or potassium alkoxide. A solvent, preferably alcohol (e.g. methanol or ethanol), is then preferably added in step (iii). For technical and economic reasons, it is preferable to use a solution of sodium or potassium alkoxide, in the corresponding alcohol, which is advantageously commercially available (e.g. sodium methoxide dissolved in methanol). Further addition of solvent can then be omitted.

In accordance with the invention, sodium or potassium alkoxides are sodium methoxide or sodium ethoxide which is preferably already dissolved in methanol or ethanol (e.g. sodium methoxide dissolved in methanol or sodium ethoxide dissolved in ethanol).

In contrast to the method described in WO-A-2009/036899, the method according to the invention may be carried out in a reaction vessel or reactor. The intermediate compounds accordingly remain in the reaction vessel or reactor over the whole reaction. In addition, there is no complex solvent change.

The reactions of steps (i), (ii) and (iii) can be conducted at standard pressure (ca. 1013 mbar). It is also possible to conduct the reaction under reduced or elevated (superatmospheric) pressure.

The reactions of steps (i), (ii) and (iii) proceed at suitable temperatures depending on the substrates used. Suitable temperatures can be determined easily by routine experiments.

For example, step (i) may be conducted at a temperature in the range from approximately −30° C. to approximately 50° C., preferably from approximately 0° C. to approximately 30° C. The reaction is particularly preferably carried out at a temperature in the range from approximately 20° C. to approximately 30° C. Step (i) is preferably carried out at a temperature in the range from approximately 20° C. to approximately 30° C. and at standard pressure, i.e. approximately 1013 mbar.

Step (ii) can be conducted, for example, at a temperature in the range from approximately 20° C. to approximately 200° C., preferably from approximately 40° C. to approximately 150° C. The reaction is particularly preferably conducted at a temperature in the range from approximately 60° C. to approximately 80° C. Step (ii) is preferably carried out at a temperature in the range from approximately 60° C. to approximately 80° C. and at standard pressure, i.e. approximately 1013 mbar.

Step (iii) can be conducted, for example, at a temperature in the range from approximately 20° C. to approximately 120° C., preferably from approximately 20° C. to approximately 100° C. The reaction is particularly preferably carried out at a temperature in the range from approximately 20° C. to approximately 80° C. Step (iii) is preferably conducted at a temperature in the range from approximately 20° C. to approximately 80° C. and at standard pressure, i.e. approximately 1013 mbar.

In the method according to the invention, the molar ratio of the compound of the formula (II) to the alkali metal hydroxide used in the alcoholic alkali metal hydroxide solution can be slightly varied. The molar ratio of alkali metal hydroxide to malonic ester should preferably be between 0.5:1 and 1.5:1, particularly preferably between 0.9:1 and 1.1:1, especially preferably 1:1. By using larger amounts of alkali metal hydroxide in proportion to the malonic ester, the unfavourable formation of a di-salt is increased. This then leads to increases in by-products and ultimately to yield losses, also in the subsequent steps.

In contrast, the molar ratio of the compound of the formula (III) to the compound of the formula (IV), or of the compound of the formula (V) to the alkali metal alkoxide of the formula (VI), may be widely varied. The molar ratios of the reactants to one another are not generally subject to any limits.

It is advantageous in step (ii) when the molar ratio of the compound of the formula (IV) to the compound of the formula (III) is in the range from 5 to 1, particularly in the range from 2 to 1. In accordance with the invention, the molar ratio is preferably in the range from 1 to 1.5.

It is advantageous in step (iii) when the molar ratio of the alkali metal alkoxide of the formula (VI) to the compound of the formula (V) is in the range from 0.5 to 10, particularly in the range from 1 to 5. In accordance with the invention, the molar ratio is preferably in the range from 1 to 1.5.

Unless otherwise stated, the term "alkyl" includes branched or unbranched hydrocarbons. Alkyl residues in the definition of the residues $R^1$ to $R^3$ are, according to the invention, $C_1$-$C_{12}$-alkyl, $C_1$-$C_6$-alkyl, $C_1$-$C_4$-alkyl or $C_1$-$C_2$-alkyl. Alkyl residues in the definition of phase transfer catalysts are, according to the invention, $C_1$-$C_{18}$-alkyl, $C_1$-$C_{12}$-alkyl, $C_1$-$C_6$-alkyl, $C_1$-$C_4$-alkyl or $C_1$-$C_2$-alkyl. Examples of such alkyls which may be used according to the invention are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

The present invention is further elucidated by way of the following examples, in which the examples are not to be interpreted in a manner which limits the invention.

PREPARATION EXAMPLE 1 (Inventive)

Preparation of sodium 4-(methoxycarbonyl)-5-oxo-2,5-dihydrofuran-3-olate and sodium 4-(ethoxycarbonyl)-5-oxo-2,5-dihydrofuran-3-olate Step (i): 2 kg (14.83 mol, 98%) of dimethyl malonate are charged at 20° C. without solvent and to this are added 967.85 g (14.83 mol, 86%) of KOH (dissolved in 4.89 kg of methanol) over 1 hour. The mixture is then stirred for 1 hour at 20° C. and subsequently methanol is distilled off under reduced pressure at an internal temperature of ca. 35° C. The residue is dewatered to remove methanol and water residues under reduced pressure by azeotroping with ca. 4 kg of xylene at 40 to 56° C. The residual xylene suspension is reacted directly in the following step.

Step (ii): After addition of 123.7 g (0.44 mol) of tetra-n-butylammonium chloride and 1.95 kg (17.8 mol) of methyl chloroacetate to the suspension from step (i), the reaction mixture obtained is heated to 60° C. and then stirred at this temperature for 5 hours. Xylene and methyl chloroacetate are then distilled off at ca. 60° C. and, following addition of ca. 1 kg of xylene and 3.7 kg of water, the organic phase is removed at ca. 45° C. and xylene and water residues distilled off under reduced pressure.

Step (iii): To the residue from step (ii) are added 2.67 kg (14.84 mol) of a 30% strength sodium methoxide solution in methanol. The suspension is initially heated to 65° C. for 2 hours, then cooled to 10° C., stirred for 1 hour at this temperature and filtered. The residue is washed with 594 g of methanol as a displacement washing and dried under reduced pressure. 2.159 kg (97.51% HPLC purity) of sodium 4-(methoxycarbonyl)-5-oxo-2,5-dihydrofuran-3-olate are obtained. Based on the dimethyl malonate used, this corresponds to an isolated yield of 79%.

$^1$H-NMR ($D_2O$, 298K) δ: 3.73 s (3H), 4.42 s (2H).

PREPARATION EXAMPLES 2-12

Step (ii):

11.95 g (75.7 mmol) of commercially supplied potassium methyl malonate are dissolved/suspended in 71.25 g of various solvents/solvent mixtures, which were varied with regard to temperatures and catalyst addition according to Table 1.

Subsequently 8.23 g (75.0 mol) of methyl chloroacetate are added and the mixtures obtained stirred at room temperature.

TABLE 1

(Experiments 2-6 non-inventive, experiments 7-12 inventive)

| Experiment | Solvent (mixture) | Addition | Temperature | Conversion (GC) |
|---|---|---|---|---|
| 2 | DMF | — | RT | >98% |
| 3 | Cyclohexane | — | RT | — |
| 4 | Toluene | — | RT | — |
| 5 | Toluene: DMF = 9:1 | — | RT | — |
| 6 | Toluene | PEG 500 | RT | — |
| 7 | Toluene | 0.18 mol % TBAB + PEG 500 | RT | 93% |
| 8 | Toluene | 0.18 mol % TBAB | RT | 93% |
| 9 | Toluene | 0.08 mol % TBAB | RT | 76% |
| 10 | Toluene | 0.18 mol % TBAB | 50° C. | >98% |
| 11 | Toluene | 0.12 mol % TBAB | 50° C. | >95% |
| 12 | ½ Toluene | 0.12 mol % TBAB | 50° C. | >98% |

TBAB: tetra-n-butylammonium bromide (phase transfer catalyst)
PEG 500: Polyethylene glycol with an average molecular mass of 500 g/mol Result: it can be seen from the experimental results of preparation examples 2 to 12 that 1. it is possible to replace the polar DMF with the non-polar toluene, in which case the addition of a phase transfer catalyst (here TBAB) is necessary. (see Exp. 2-8),
2. the lower limit of the phase transfer catalyst addition is preferably ~0.1 mol %, and
3. a temperature increase is advantageous.
4. Comparison with the method according to the prior art (WO-A-2009/036899): Examples 2 and 4 are carried out according to methods of WO-A-2009/036899. Example 2 with the polar solvent DMF and example 4 with the non-polar solvent toluene. The comparison of example 4 (according to WO-A-2009/036899) and example 8 (inventive) shows that the change of solvent from polar to non-polar requires the use of a phase transfer catalyst, as otherwise no conversion to the product takes place. The comparison of example 2 (according to WO-A-2009/036899) using polar solvent and example 8 (inventive) shows that in the reaction in the two-phase method according to the invention comparable conversions to those in the method according to WO-A-2009/036899 can be achieved. Owing to the biphasicity of the method according to the invention, however, the separation and isolation of the product is considerably simpler to carry out than in the one-phase method according to WO-A-2009/036899 using the polar solvent.

PREPARATION EXAMPLE 13 (with Toluene)
(Inventive)

Step (i): 4150 g of methanol are initially charged in a reactor and 1858 g (29 mol; 86%) of solid potassium hydroxide are added gradually with vigourous stirring and with cooling, to give a 30% strength solution of KOH in methanol. This is charged to a solution of 3839 g (29 mol) of dimethyl malonate in 5700 g of toluene and added over the course of 1 h with vigourous stirring. The reaction mixture is then stirred for 2-4 h at room temperature. A further 5700 g of toluene are then added and methanol distilled off until no further methanol is observable in the bottom filtrate. (GC peak area <0.1%).

Step (ii): 96 g (0.3 mol) of tetrabutylammonium bromide (TBAB) are added to the suspension of potassium methyl malonate in toluene from step (i) and heated to 65° C. 2655 g (24.5 mol) of methyl chloroacetate are then added and the reaction mixture stirred for at least 6 h at 65° C. After completion of the reaction the mixture is cooled and extracted with 6540 g of water. The toluene phase is distilled so that approximately half of the toluene is distilled off and the water is removed.

Step (iii): The toluene solution is brought to 60° C. and treated with 5010 g of NM30 solution (sodium methoxide). After completion of the addition, the reaction mixture is stirred for a further 4 h at ca. 60° C.

The reaction mixture is cooled for at least 2 h to <5° C. The precipitated product is filtered off and washed twice with 1500 g methanol each time and dried.

Yield: 74.6% (purity (HPLC): 94.5%)

PREPARATION EXAMPLE 14 (With Xylene)
(Inventive)

The synthesis is carried out analogously to that in preparation example 13, but xylene is used instead of toluene.

Yield: 57.7% (purity (HPLC): 95.8%).

The invention claimed is:

1. Method for preparing an alkali metal salt of a 4-hydroxy-2-oxo-2,5-dihydrofuran-3-carboxylic ester of formula (I)

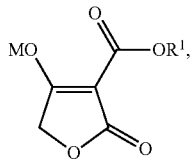

(I)

comprising:
(i): reacting a malonic ester of formula (II)

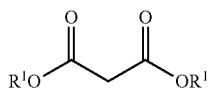

(II)

with an alcoholic alkali metal hydroxide solution to give the corresponding malonic ester mono-alkali metal salt of formula (III)

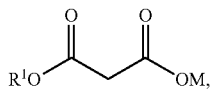

(III)

(ii): reacting a malonic ester monoalkali metal salt of formula (III) from (i) with a chloroacetic ester of formula (IV)

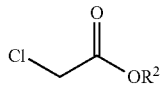

(IV)

in the presence of at least one phase transfer catalyst to give a compound of formula (V)

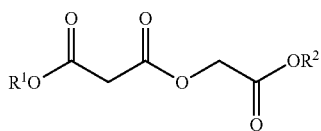

(V)

wherein the phase transfer catalyst is an organic ammonium or phosphonium salt, (iii): reacting a compound of formula (V) by addition of an alkali metal alkoxide of formula (VI)

M'OR³   (VI)

in a ring closure reaction as a result of which the alkali metal salt of 4-hydroxy-2-oxo-2,5-dihydrofuran-3-carboxylic ester of formula (I) is produced, where in said formulae (I) to (VI)

$R^1$, $R^2$ and $R^3$ are each independently $C_1$-$C_{12}$-alkyl;

M and M' are each independently an alkali metal in a corresponding oxidation state.

2. Method according to claim 1, in which (i) is carried out in the presence of an aromatic hydrocarbon or in which an aromatic hydrocarbon is added to reaction mixture during or after (i).

3. Method according to claim 2, in which a reaction in (i) is conducted in the presence of water.

4. Method according to claim 2, in which alcohol and optionally water are at least partially removed from a reaction mixture on completion of (i), wherein the malonic ester monoalkali metal salt of formula (III) is then present as a suspension in an aromatic hydrocarbon.

5. Method according to claim 1, where $R^1$, $R^2$ and $R^3$ are in each case methyl or ethyl; and M and M' are in each case sodium or potassium in a corresponding oxidation state.

6. Method according to claim 1, wherein an alcoholic alkali metal hydroxide solution used in (i) is a methanolic or ethanolic potassium hydroxide solution or methanolic or ethanolic sodium hydroxide solution, which, based on the amount of sodium hydroxide or potassium hydroxide used, is used as a solution up to 30% by weight.

7. Method according to claim 6, wherein an aromatic hydrocarbon from (i) is xylene or toluene and the water and alcohol present in a reaction mixture are removed from the reaction mixture by distillation.

8. Method according to claim 7, wherein the solvent is toluene and the alcohol present in the reaction mixture and the water present are removed by azeotropic distillation.

9. Method according to claim 7, wherein the water present in the reaction mixture in (i) is removed by addition of xylene and subsequent azeotropic distillation, but wherein the alcohol present in the reaction mixture is initially removed by distillation.

* * * * *